United States Patent [19]

Wu et al.

[11] 4,158,022

[45] Jun. 12, 1979

[54] PREPARATION OF ETHYLBENZENE HYDROPEROXIDE

[75] Inventors: Ching-Yong Wu, O'Hara Township, Allegheny County; Harold E. Swift, Gibsonia; John E. Bozik, Plum Borough, all of Pa.

[73] Assignee: Gulf Research & Development Company, Pittsburgh, Pa.

[21] Appl. No.: 855,742

[22] Filed: Nov. 29, 1977

Related U.S. Application Data

[63] Continuation-in-part of Ser. No. 746,246, Dec. 1, 1976, abandoned.

[51] Int. Cl.² ............................................. C07C 179/02
[52] U.S. Cl. ..................................................... 568/571
[58] Field of Search .................................... 260/610 B

[56] References Cited

U.S. PATENT DOCUMENTS

| | | | |
|---|---|---|---|
| 2,632,774 | 3/1953 | Conner et al. | 260/610 B |
| 2,867,666 | 1/1959 | Erickson et al. | 260/610 B |
| 3,187,055 | 6/1965 | Armstrong | 260/610 B |
| 3,647,886 | 3/1972 | Mead et al. | 260/610 B |

FOREIGN PATENT DOCUMENTS

676722  8/1952  United Kingdom ................. 260/610 B

*Primary Examiner*—Werren B. Lone

[57] ABSTRACT

Ethylbenzene hydroperoxide is prepared by the oxidation of ethylbenzene with molecular oxygen in the presence of a minute amount of solid barium oxide.

10 Claims, No Drawings

PREPARATION OF ETHYLBENZENE HYDROPEROXIDE

This application is a continuation-in-part of our application Ser. No. 746,246, filed Dec. 1, 1976 now abandoned.

FIELD OF THE INVENTION

This invention relates to ethylbenzene hydroperoxide and more particularly it relates to the preparation of ethylbenzene hydroperoxide by the oxidation of ethylbenzene using molecular oxygen in the presence of a catalyst.

DESCRIPTION OF THE PRIOR ART

U.S. Pat. No. 2,867,666 describes the preparation of ethylbenzene hydroperoxide from ethylbenzene by oxidation of the ethylbenzene with molecular oxygen. The specification states that it is essential that a basic substance be employed in the reaction mixture because practically no oxidation occurs in its absence. A suitable quantity of the basic substance is specified to be in the range of 0.5 to 10 weight percent and barium oxide is listed as one of the suitable basic substances.

SUMMARY OF THE INVENTION

We have discovered a catalyzed process for the preparation of ethylbenzene hydroperoxide by the oxidation of ethylbenzene with molecular oxygen in which the yield of ethylbenzene hydroperoxide as well as the selectivity to ethylbenzene hydroperoxide is substantially increased. More particularly, we have discovered that these benefits result when ethylbenzene is oxidized in the presence of a minute amount of barium oxide.

Certain hydrocarbons can be oxidized to the hydroperoxide by direct oxidation using molecular oxygen. In particular, hydrocarbons having a hydrogen atom on a tertiary carbon atom are relatively easy to oxidize to a hydroperoxide in good yield. Other hydrocarbons are more difficult to oxidize to the hydroperoxide and the resulting hydroperoxide is itself quite unstable. Cumene which contains both a tertiary carbon atom and an aromatic ring is comparatively easy to oxidize and can be directly oxidized to concentrations as high as 50 percent and higher. Furthermore, according to Lloyd in *Methods in Free Radical Chemistry*, Vol. 4, edited by Huyser (1973), cumene hydroperoxide decomposes at a temperature above 80° C. As a result of this stability, cumene hydroperoxide is the only aromatic hydroperoxide which has been commercially available.

In striking contrast with cumene and cumene hydroperoxide, ethylbenzene and ethylbenzene hydroperoxide exhibit substantial differences in chemical properties. For example, ethylbenzene is difficult to oxidize with molecular oxygen and is oxidized to a relatively low concentration of ethylbenzene hydroperoxide. Furthermore, the resulting ethylbenzene hydroperoxide has a low degree of stability. For example, ethylbenzene hydroperoxide concentrated by distillation to a concentration of 40 percent in ethylbenzene is unstable at room temperature (20°-25° C.). As a result of this relative instability, solutions containing a desirable concentration of ethylbenzene hydroperoxide generally include significant quantities of co-products, such as 1-phenylethanol and acetophenone.

In Pat. No. 2,867,666 barium oxide has been included in a list of basic substances stated to be essential for the oxidation of ethylbenzene to ethylbenzene hydroperoxide. We have, in fact, ascertained that barium oxide, when used in moderate amounts, does increase the production of ethylbenzene hydroperoxide and in even larger amounts decreases the amount of ethylbenzene hydroperoxide as compared with the amount resulting in the absence of barium oxide. But in addition we have surprisingly discovered that barium oxide actively catalyzes the decomposition of ethylbenzene hydroperoxide. In view of this discovery, we have more surprisingly made the further discovery that optimum selectivity to ethylbenzene hydroperoxide occurs in the presence of a minute amount of barium oxide, and not in its absence.

When ethylbenzene is oxidized to ethylbenzene hydroperoxide, the primary aromatic by-products are acetophenone and 1-phenylethanol. Although these by-products can theoretically be converted to ethylbenzene for recycle, the economics of this recovery operation would, in general, prohibit its use in commercial scale. Therefore, these aromatic by-products represent a process loss. Additionally, the nonaromatic by-products and also the total oxidation to carbon dioxide and water represents a process loss. Generally, the fuel value of these organic by-products represents their true value in the process. Therefore, in carrying out the oxidation reaction of ethylbenzene, it is most desirable to reduce the losses, if possible, without reducing the yield of the desired ethylbenzene hydroperoxide. By our invention we have unexpectedly discovered that maximum yield and maximum selectivity to ethylbenzene hydroperoxide can be concurrently induced when a minute amount of barium oxide, that is a minimum amount of about 0.005 weight percent and a maximum amount of about 0.15 weight percent, is present during the oxidation reaction. It is highly unexpected that barium oxide is a catalyst for the desired reaction in these minute amounts while it functions overall as a decomposition catalyst in the larger amounts. Furthermore, this is unexpected because it is contrary to general experience to find selectivity and yield in a chemical reaction concurrently reaching a maximum at the same reaction conditions. It is additionally unexpected in view of U.S. Pat. No. 2,867,666 because this patent specifies a range of 0.5 to 10 weight percent of the base such as barium oxide as being suitable.

In our procedure for preparing ethylbenzene hydroperoxide with barium oxide catalyst, the barium oxide is preferably introduced into the reactor as a finely divided powder in order to accelerate its dispersion throughout the liquid and hasten its availability as a catalyst. Therefore, it is preferred that the initial particle size be small enough to stay in suspension in the liquid phase. However, larger sized particles of barium oxide even including pellet size can be used since the stirring or agitation of the reactor contents will gradually break down and disperse the barium oxide, including this larger sized barium oxide, throughout the solution. Therefore, the initial particle size of the barium oxide can broadly range from about 20 microns to about 5 millimeters in diameter and preferably a particle size ranging between about 50 and about 1,000 microns is used.

When the solution containing the powdered barium oxide is heated up under agitation, a fairly rapid, distinct change in appearance occurs at about 120°-125° C. This change can be described as a transition from a powdery appearance to a milky appearance. This transition to a milky solution is followed by the oxidation reaction, indicative of some type of interaction, probably physical, between the barium oxide and the organic phase to form a more intimate association. We believe that this transition is related to the unexpected catalytic effect exhibited by barium oxide. The experimental data suggests to us that a minute amount of the barium oxide is involved in this transition and that it is this barium oxide that is responsible for the positive catalytic effect and the concomitant increased selectivity. The experimental data further suggests that more than a minute amount of barium oxide is not involved in this transition but remains in solid particulate form and that it is this solid barium oxide that is responsible for the negative, decomposition effect.

This transition to a milky solution upon heating this organic solution containing dispersed barium oxide and these catalytic effects are believed to be unique with barium oxide since they are not observed with conventional bases, such as solid sodium hydroxide which does not exhibit a significant catalytic effect. When the stirring of this milky solution is stopped while the elevated temperature is maintained, the solution retains its milky appearance. When the unstirred solution is cooled to room temperature, it reverts to its powdery appearance and the barium oxide precipitates out, resulting in a clear solution. The oxidation reaction is carried out under anhydrous conditions since the presence of water results in lowered selectivity as well as a reduced rate of oxidation.

In order to obtain beneficial results in accordance with our invention, a minute amount of barium oxide is used for the oxidation of ethylbenzene to ethylbenzene hydroperoxide. Significant improvement in yield and selectivity to ethylbenzene hydroperoxide results when barium oxide is used in an amount as low as about 0.0005 weight percent based on the ethylbenzene, but we prefer that at least about 0.001 percent barium oxide be used for a more significant improvement and we most prefer that at least about 0.002 be used. The maximum amount of barium oxide to obtain the desired catalytic effect of this invention should not exceed about 0.15 weight percent although higher amounts can be used, if desired, at reduced selectivity and yield. We prefer that the maximum amount of barium oxide does not exceed about 0.1 weight percent and most prefer that it not exceed 0.04. Since the barium oxide catalyzes the decomposition of the ethylbenzene hydroperoxide, it is desirable to remove the barium oxide from the ethylbenzene hydroperoxide following its preparation.

In the oxidation of ethylbenzene to ethylbenzene hydroperoxide, both the reaction rate and the product stability are a function of temperature. The temperature of the reactant ethylbenzene solution can conveniently be as low as 120° C., but we prefer that it be at least about 125° C. for a suitable rate of reaction. The maximum temperature should not exceed about 150° C. because of the greatly increasing instability of the product ethylbenzene hydroperoxide at the higher temperatures. We prefer that the reaction temperature not exceed about 140° C.

The oxidation of the ethylbenzene by our procedure can conveniently be carried out in a batch reaction in which the molecular oxygen is bubbled through the ethylbenzene solution at an appropriate elevated temperature and pressure. A suitable elevated pressure is required, sufficient to maintain the ethylbenzene in solution at the temperature of reaction. Any suitable source of molecular oxygen, such as air or pure oxygen, can be used. When the oxygen is mixed with diluent gas, it is important that the diluent be free of any reactive contaminant gas, such as a nitrogen oxide or an oxide of sulfur, which would adversely react with one or more of the components in the reaction vessel. The partial pressure of oxygen in the reaction vessel is not critical. We prefer that the partial pressure of oxygen in the reaction zone be at least about 10 psia (68.9 kPa) but a partial pressure of oxygen as low as about 5 psia (34.5 kPa) is useful. The partial pressure of oxygen can be as high as about 200 psia (1,376 kPa) or even higher, but we prefer that the partial pressure be no greater than about 50 psia (344 kPa).

It is desirable that a minor amount of a hydrocarbon hydroperoxide be initially present in the ethylbenzene to eliminate the substantial induction time required to initiate the oxidation reaction and therefore to substantially increase the rate of oxidation in the early phase of the oxidation reaction. This hydroperoxide is desirably used in an amount up to about 5 weight percent based on the ethylbenzene used. Higher amounts can be present but do not exert an additional beneficial effect. It is preferred to use at least about 0.5 weight percent of the initiator hydroperoxide. Most preferably the hydroperoxide initiator is the same hydroperoxide that is produced in the reaction, namely, ethylbenzene hydroperoxide, however, any suitable hydrocarbon hydroperoxide can be used including both aromatic and paraffinic hydroperoxides. Suitable hydroperoxide initiators include cumene hydroperoxide, isobutane hydroperoxide, isopentane hydroperoxide, and the like.

DESCRIPTION OF PREFERRED EMBODIMENTS

In the following examples the ethylbenzene contained no reactive impurities and a maximum of 1.0 weight percent inert hydrocarbon isomers. The barium oxide, BaO, was 97.5 percent pure with barium carbonate and strontium oxide comprising the major impurities and was used as a 60–80 mesh powder. The air was dried to remove water and treated to remove carbon dioxide. The isobutane hydroperoxide used as an initiator contained 70 percent of the hydroperoxide in t-butanol. A 300 milliliter glass reactor with stirrer and heating jacket was used for these experiments. The initial and product samples were analyzed for hydroperoxide concentration by standard iodometric titration. The initial finite hydroperoxide measurement resulted from the hydroperoxide initiator plus a minor amount of oxidation that occured before analysis could be accomplished.

Analysis of the by-products was carried out in a gas-liquid chromatograph using a carbowax column or in a high performance liquid chromatograph. In the gas-liquid chromatograph analysis all of the ethylbenzene hydroperoxide was pyrolyzed to acetophenone and 1-phenylethanol. The analysis determined ethylbenzene, acetophenone and 1-phenylethanol. The by-product, acetophenone and 1-phenylethanol, was determined by difference in conjunction with the titration analysis for ethylbenzene hydroperoxide. The high performance chromatograph analysis did not decompose the ethylbenzene hydroperoxide since it was carried out at room temperature (20°–25° C.), therefore, it gave a direct analysis of the by-products.

EXAMPLES 1-4

Ethylbenzene hydroperoxide was prepared in a series of experiments. In the first experiment 100 ml. ethylbenzene were heated to 135° C. in a reactor. Five ml. of isobutane hydroperoxide initiator were added. Air was then bubbled through the reaction at a rate of 100 cc./per minute and a pressure of 140 psig. (965 kPa). The concentration of ethylbenzene hydroperoxide (EBHP) was determined at 30 minute intervals. This procedure was repeated several times except that 0.5 g. of sodium hydroxide, barium hydroxide or barium oxide was used under anhydrous conditions. The results of these experiments are set out in Table I.

Table I

| | Ethylbenzene Hydroperoxide Conc. % | | | |
|---|---|---|---|---|
| Example Time, hrs. | 1 No Base | 2 NaOH | 3 Ba(OH)$_2$ | 4 BaO |
| 0 | 3.1 | 3.2 | 3.1 | 3.0 |
| 0.5 | 6.9 | 5.3 | 7.4 | 7.1 |
| 1.0 | 9.1 | 7.7 | 10.1 | 11.4 |
| 1.5 | 10.4 | 9.5 | 12.1 | 14.3 |
| 2.0 | 11.0 | 10.5 | 13.5 | 16.0 |
| 2.5 | 10.8 | 10.7 | 14.5 | 16.9 |
| 3.0 | 10.8 | 10.8 | 14.4 | 17.2 |

EXAMPLE 5

The effect of barium oxide on ethylbenzene hydroperoxide was studied at room temperature. Ethylbenzene was oxidized to a reaction product containing ethylbenzene hydroperoxide. Pure ethylbenzene hydroperoxide was obtained by extracting this reaction product with 10 percent aqueous sodium hydroxide. The aqueous solution containing the sodium salt of ethylbenzene hydroperoxide was reacted with gaseous carbon dioxide until the pH went below 9.0 to liberate pure ethylbenzene hydroperoxide. Analysis of the purified ethylbenzene hydroperoxide by high performance liquid chromatography indicated that a trace of acetophenone was the only remaining impurity.

The purified ethylbenzene hydroperoxide was made up into a 3.5 percent solution in ethylbenzene and 100 ml. of this solution was charged to a glass reactor. A small sample from the reactor was titrated iodometrically to determine the initial concentration of ethylbenzene hydroperoxide. The desired quantity of powdered barium oxide was added and the reactor was pressured to 50 psi. (0.34 MPa) with nitrogen. After stirring for five minutes at room temperature, the solution was titrated to determine the final concentration of ethylbenzene hydroperoxide (EBHP). The results from a series of experiments are tabulated in Table II.

Table II

| BaO, % | EBHP, % initial | EBHP, % final | % EBHP decomposed |
|---|---|---|---|
| 0 | 3.45 | 3.45 | 0 |
| 0.010 | 3.51 | 3.43 | 2.3 |
| 0.033 | 3.65 | 3.60 | 1.4 |
| 0.1 | 3.65 | 3.52 | 3.6 |
| 0.2 | 3.64 | 3.40 | 6.6 |
| 0.67 | 3.45 | 3.03 | 12.2 |
| 1.67 | 3.60 | 2.97 | 17.5 |
| 5.0 | 3.34 | 0.71 | 78.7 |

EXAMPLE 6

The oxidation of ethylbenzene to produce ethylbenzene hydroperoxide was studied using various amounts of barium oxide. The oxidation reaction was carried out in a 300 ml. glass reactor maintained in a constant temperature bath equipped with a magnetic stirrer, a gas bubbling tube and a dip tube for sampling. In each experiment 100 ml. of ethylbenzene, five ml. of 70 percent isobutane hydroperoxide and a desired amount of finely divided barium oxide catalyst were charged to the reactor. Air was then bubbled through the reaction mixture at a rate of 100 cc. per minute and a pressure of 140 psi. (965 kPa). The stirrer was started and the reactor was heated to 135° C. for three hours.

The reaction product was analyzed by iodometric titration and by gas-liquid chromatograph. The analysis of the experiment using 0.1 percent barium oxide is set forth as typical. Iodometric titration of the reaction product disclosed 18.75 percent ethylbenzene hydroperoxide. Since most of the isobutane hydroperoxide initiator is decomposed during the reaction, the analysis for ethylbenzene hydroperoxide will include only a trace of isobutane hydroperoxide. The gas-liquid chromatograph analysis resulted in 78.89 percent ethylbenzene, 12.78 percent acetophenone, 5.58 percent 1-phenylethanol and 2.78 percent other products comprising primarily t-butanol from the decomposition of the isobutane hydroperoxide initiator. These analyses indicated a conversion of 21.1 percent and a selectivity to ethylbenzene hydroperoxide of 88.9 percent. When pure ethylbenzene hydroperoxide was pyrolyzed in the gas-liquid chromatograph, the analysis showed 56 percent acetophenone, 21 percent 1-phenylethanol with the balance assumed to be oxygen and water which were not determined. With this data the selectivity to acetophenone and 1-phenylethanol was determined to be 5.7 percent and 5.4 percent, respectively. The results of these analyses are set out in Table III which lists the yield of ethylbenzene hydroperoxide (EBHP), the conversion of ethylbenzene and the selectivity to ethylbenzene hydroperoxide, acetophenone (AP) and 1-phenylethanol (PE).

Table III

| BaO, % | EBHP, % | Conv. % | Selectivity, % | | |
|---|---|---|---|---|---|
| | | | EBHP | AP | PE |
| 0[1] | 11.41 | 13.72 | 83.4 | 8.2 | 6.0 |
| 0.0013[1] | 19.28 | 21.03 | 91.7 | 4.8 | 4.0 |
| 0.0033[2] | 19.2 | 19.62 | 97.9 | [3] | [3] |
| 0.0067[1] | 20.1 | 21.08 | 95.4 | [3] | [3] |
| 0.010 | 18.01 | 19.68 | 91.5 | [3] | [3] |
| 0.020 | 19.17 | 20.25 | 94.7 | [3] | [3] |
| 0.033 | 18.98 | 20.93 | 90.7 | 5.2 | 4.0 |
| 0.10 | 18.75 | 21.10 | 88.9 | 5.7 | 5.4 |
| 0.20 | 17.32 | 21.11 | 82.2 | 14.0 | 3.5 |
| 0.67 | 16.56 | 24.8 | 66.7 | 24.0 | 8.9 |
| 1.67 | 9.43 | 21.0 | 45.0 | 45.4 | 9.6 |
| 5.0 | 0.34 | 9.0 | 3.8 | 60.3 | 35.9 |

[1]average of two experiments
[2]average of three experiments
[3]too small to be determined accurately.

According to the data in Table III the conversion of ethylbenzene substantially diminishes in the presence of large amounts of barium oxide. We believe that this is the result of a diminished amount of hydroperoxide initiator which is decomposed by the excess barium oxide as shown in Example 5. This conclusion is suggested, in particular by the last experiment using five percent barium oxide in which about 3.5 percent hydroperoxide is introduced as an initiator and less than one percent hydroperoxide is present in the reaction product.

Even though the oxidation of ethylbenzene to ethylbenzene hydroperoxide in the presence of barium oxide is carried out under substantially anhydrous conditions preferably including the use of dried air and predried ethylbenzene, it is recognized that very low concentrations of water will result when minor amounts of co-product acetophenone are produced. It is believed that most of this water of reaction leaves the system but some of this water of reaction may react with the barium oxide to form a minor amount of barium hydroxide. Since barium hydroxide is an inferior catalyst for the oxidation of ethylbenzene to ethylbenzene hydroperoxide, its presence is not desired. Advantageously, the present procedure of using a minute amount of barium oxide to obtain maximum selectivity results in less by-product water and therefore less of the inferior barium hydroxide in the reactor. As used herein, the expression "substantially anhydrous barium oxide" contemplates barium hydroxide as a possible minor component, while "substantially anhydrous conditions" refers to the substantial absence of free water.

It is to be understood that the above disclosure is by way of specific example and that numerous modifications and variations are available to those of ordinary skill in the art without departing from the true spirit and scope of the invention.

We claim:

1. A process for oxidizing ethylbenzene to ethylbenzene hydroperoxide comprising heating ethylbenzene in contact with about 0.0005 to about 0.15 weight percent barium oxide at a temperature between about 120° C. and about 150° C. under substantially anhydrous conditions and contacting said ethylbenzene with molecular oxygen whereby said ethylbenzene is oxidized to ethylbenzene hydroperoxide at improved selectivity and yield.

2. A process for oxidizing ethylbenzene to ethylbenzene hydroperoxide in accordance with claim 1 in which the oxidation reaction is carried out in the presence of between about 0.001 percent and about 0.1 weight percent barium oxide.

3. A process for oxidizing ethylbenzene to ethylbenzene hydroperoxide in accordance with claim 1 in which the oxidation reaction is carried out in the presence of between about 0.002 percent and about 0.04 weight percent barium oxide.

4. A process for oxidizing ethylbenzene to ethylbenzene hydroperoxide in accordance with claim 1 in which the partial pressure of oxygen is between about 5 and about 200 psia.

5. A process for oxidizing ethylbenzene to ethylbenzene hydroperoxide in accordance with claim 1 in which the ethylbenzene is contacted with air.

6. A process for oxidizing ethylbenzene to ethylbenzene hydroperoxide in accordance with claim 1 in which a minor amount of a hydrocarbon hydroperoxide initiator is present in the reaction mixture.

7. A process for oxidizing ethylbenzene to ethylbenzene hydroperoxide in accordance with claim 6 in which the initiator is ethylbenzene hydroperoxide.

8. A process for oxidizing ethylbenzene to ethylbenzene hydroperoxide in accordance with claim 1 in which the temperature is between about 125° C. and about 140° C.

9. A process for oxidizing ethylbenzene to ethylbenzene hydroperoxide in accordance with claim 1 in which the barium oxide is in a particle size of about 20 microns to about 5 millimeters in diameter and said mixture of ethylbenzene and barium oxide is agitated.

10. A process for oxidizing ethylbenzene to ethylbenzene hydroperoxide in accordance with claim 9 in which the barium oxide is in a particle size of about 50 to about 1,000 microns.